US00PP22446P2

(12) United States Plant Patent
Shlevin

(10) Patent No.: US PP22,446 P2
(45) Date of Patent: Jan. 3, 2012

(54) ***CANNA* PLANT NAMED 'CHOCOLATE SUNRISE'**

(50) Latin Name: *Canna×generalis*
Varietal Denomination: CHOCOLATE SUNRISE

(76) Inventor: Eliyahu Shlevin, Kibbutz Saad (IL)

( * ) Notice: Subject to any disclaimer, the term of this patent is extended or adjusted under 35 U.S.C. 154(b) by 0 days.

(21) Appl. No.: 12/803,914

(22) Filed: Jul. 8, 2010

Related U.S. Application Data

(60) Provisional application No. 61/270,756, filed on Jul. 14, 2009.

(51) Int. Cl.
*A01H 5/00* (2006.01)

(52) U.S. Cl. ..... Plt./415

(58) Field of Classification Search ..... Plt./415
See application file for complete search history.

*Primary Examiner* — June Hwu
*Assistant Examiner* — Louanne Krawczewicz Myers

(57) ABSTRACT

A new and distinct cultivar of *Canna* plant named 'CHOCOLATE SUNRISE' that is characterized by dwarf habit, olive green to purple brown foliage, and deep yellow flowers which are open faced and attractively arranged within the inflorescence. In combination these traits set 'CHOCOLATE SUNRISE' apart from all other varieties of *Canna* known to the inventor.

1 Drawing Sheet

Genus: *CANNA*.
Species: ×*generalis*.
Denomination: 'CHOCOLATE SUNRISE'.

BACKGROUND OF THE INVENTION

This application is co-pending with the application of same filing date for the inventor's variety of *Canna* plant named 'ORANGE CHOCOLATE' (U.S. Plant patent application Ser. No. 12/803,912).

The present invention relates to a new and distinct cultivar of *Canna*, also known as *Canna* Lily or Indian Shot, which is grown as an ornamental annual or perennial, according to climate zone, for use in planted containers and in the garden and landscape. The new cultivar is known botanically as *Canna×generalis*, and will be referred to hereinafter by the cultivar name 'CHOCOLATE SUNRISE'.

The inventor has carried out a *Canna* breeding program at the inventor's nursery in Kibbutz Saad, Israel since 2005. The breeding program is aimed at producing new varieties of *Canna* with useful commercial characteristics: primarily new varieties which exhibit a dwarf habit with colorful foliage and bearing well-presented flowers. 'CHOCOLATE SUNRISE' arose and was selected by the inventor in 2006 as an open pollinated seedling whose male parent is unknown and whose female parent is *Canna* 'Wine and Roses' (unpatented). The inventor used this same parentage to develop the inventor's co-pending variety 'ORANGE CHOCOLATE'. Both co-pending varieties exhibit almost identical habit and foliage color. However, the flowers of 'CHOCOLATE SUNRISE' are deep yellow in color, whereas the flowers of 'ORANGE CHOCOLATE' are bright orange in color.

'CHOCOLATE SUNRISE' was first asexually reproduced by the inventor in Kibbutz Saad, Israel in 2006. Asexual propagation was accomplished by division of the rhizome. Since that time, under careful observation, the distinguishing characteristics of 'CHOCOLATE SUNRISE' have been determined stable and uniform, and to reproduce true to type in successive generations of asexual propagation.

The variety of *Canna* which is considered by the inventor to most closely resemble 'CHOCOLATE SUNRISE' is the parent plant, *Canna* 'Wine and Roses'. 'Wine and Roses' and 'CHOCOLATE SUNRISE' both exhibit dark olive green to purple brown colored foliage. However, the height of 'Wine and Roses' is approximately 75 cm-90 cm, whereas the height of 'CHOCOLATE SUNRISE' is 60 cm-80 cm. In addition, the flowers of 'Wine and Roses' are rose pink in color whereas the flowers of 'CHOCOLATE SUNRISE' are deep yellow in color.

SUMMARY OF THE INVENTION

The distinguishing characteristics of 'CHOCOLATE SUNRISE' are as follows: In combination these traits set 'CHOCOLATE SUNRISE' apart from all other existing varieties of *CANNA* known to the inventor. 'CHOCOLATE SUNRISE' has not been tested under all possible conditions and phenotypic differences may be observed with variations in environmental, climatic, and cultural conditions.

1. 'CHOCOLATE SUNRISE' grows and remains short in height.
2. After one year of growth, a plant of 'CHOCOLATE SUNRISE' achieves a height of approximately 60 cm-80 cm and a spread of 40 cm-60 cm.
3. 'CHOCOLATE SUNRISE' bears deep yellow flowers.
4. The flowers of 'CHOCOLATE SUNRISE' are open faced and attractively arranged within the inflorescence.
5. The foliage of 'CHOCOLATE SUNRISE' is dark olive green to purple brown in color.

DESCRIPTION OF THE DRAWING

The accompanying color drawing illustrates the overall appearance of 'CHOCOLATE SUNRISE' showing the color of the inflorescence and the foliage as true as it is reasonably possible to obtain in colored reproductions of this type.

The drawing labeled as FIG. 1 depicts a one year old plant of 'CHOCOLATE SUNRISE' growing in a greenhouse in Kibbutz Saad, Israel.

BOTANICAL DESCRIPTION OF THE PLANT

Figure 1:
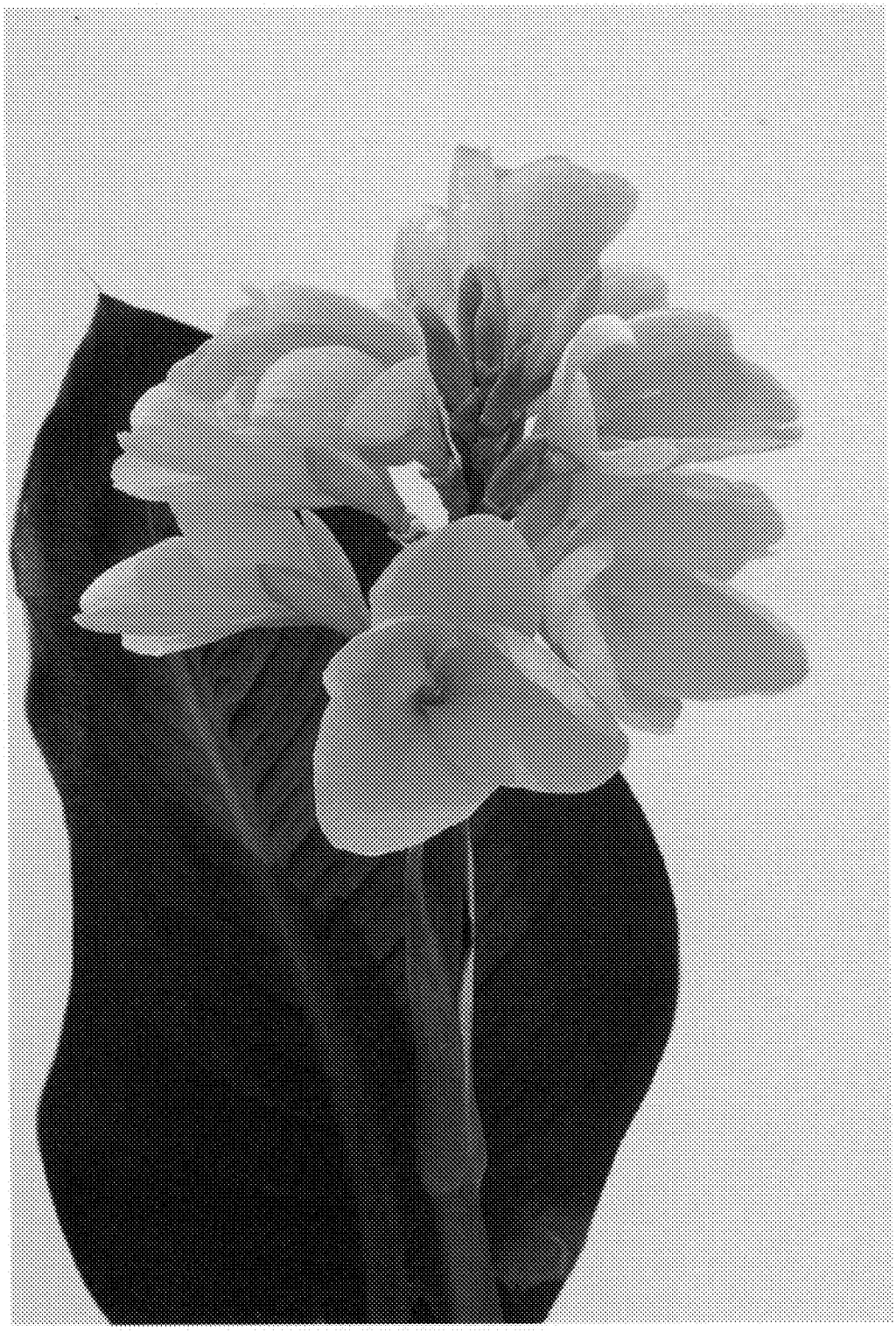

In the following botanical description, all color references are made to The Royal Horticultural Society Colour Chart, 2007 Edition, except where general terms of ordinary dictionary significance are used.

The plants used for this botanical description were grown from rhizomes which the inventor shipped from his nursery at Kibbutz Saad, Israel to Santa Barbara, Calif. The rhizomes were planted in the ground in August 2010. The observed plants were twelve months of age.

Botanical classification: *CANNA×generalis* 'CHOCOLATE SUNRISE'.

Parentage: Open pollination between unknown male parent and *Canna* 'Wine and Roses' as female parent.

Propagation: By division of field-grown rhizomes or by division of tissue cultured plants.

Cultural suggestions: In common with *Cannas* generally, 'CHOCOLATE SUNRISE' is evergreen in warm climates, but will die back as winter approaches in cool climates. Rhizomes may be mulched to protect from light frost but should be lifted and stored if the ground is liable to freeze below the surface.

Hardiness: 'CHOCOLATE SUNRISE' is evergreen in USDA Zone 8.

Heat tolerance: Plants grow and flower rapidly in sunny positions but benefit from light shade from extreme heat.

Pest and disease resistance or susceptibility: 'CHOCOLATE SUNRISE' has not been found to be more or less resistant or susceptible to the pests and diseases which affect the genus and its cultivars.

Plant form: Upright, very compact with very short multiple stems.

Rhizome description: Thick, fibrous, 3 cm-5 cm in diameter, with papery scales which are light brown 166C in color when first forming, becoming dark brown 200B as they age and peel away from the rhizome whose revealed surface is smooth, cream 11D.

Plant height: 60 cm-80 cm.

Plant spread: 40 cm-60 cm.

Branching: Average 5 basal shoots in first growing season.

Stem (each basal shoot):

- *Length.*—24 cm.
- *Diameter.*—1.2 cm.
- *Internode length.*—12 cm (measured between soil level and first node). Peduncle begins at first above-ground node.
- *Strength.*—Strong.
- *Texture.*—Glabrous.
- *Color.*—195A.

Foliage: Leaves simple, entire, sessile.

- *Leaf arrangement.*—Alternate.
- *Leaf length.*—21 cm-22 cm.
- *Leaf diameter.*—12 cm-14 cm.
- *Shape.*—Ovate.
- *Apex.*—Acute.
- *Base.*—Obtuse.
- *Margin.*—Entire.
- *Texture.*—Glabrous.
- *Luster.*—Upper surface dull, lower surface semi-glossy.
- *Venation.*—Pinnate.
- *Venation color* (*upper*).—N187A.
- *Venation color* (*lower*).—187B.
- *Leaf color* (*upper surface*).—200B.
- *Leaf color* (*lower surface*).—147A.

Petioles:

- *Arrangement.*—Sheathing.
- *Length.*—13 cm-17 cm.
- *Texture.*—Glabrous.
- *Color, upper surface.*—147B.
- *Color, lower surface.*—152B.

Inflorescence:

- *Panicle height.*—18 cm, diameter 13 cm-15 cm.
- *Inflorescence number per lateral branch.*—One.
- *Typical and observed number of flowers per inflorescence.*—17 on average.
- *Typical and observed number of inflorescences per plant.*—5.
- *Form.*—Terminal raceme with single flower opening first followed by the formation and flowering of secondary racemes. The flowers in secondary are borne in pairs on short pedicels. Each flower or pair of flowers is subtended by a single bract.
- *Natural flowering season.*—Summer months.

Flower:

- *Flower longevity on the plant.*—2 to 3 days.
- *Fragrance.*—None.
- *Flower height.*—5.5 cm.
- *Flower width.*—8 cm.
- *Buds.*—Length: 4.5 cm. Diameter: 0.8 cm. Shape: Oblong. Color: 23A.
- *Petals.*—Arrangement: 3 each, arranged in a whorl, fused at base. Length: 3.3 cm-3.6 cm. Diameter: 1.2 cm-1.6 cm. Shape: Long, elliptical. Apex: Acute. Margin: Entire. Texture: Glabrous. Color (both surfaces): Center 24B, outer and margin 41B.
- *Sepals.*—Shape: Obovate. Margin: Entire. Arrangement: 3 each, arranged in a whorl, fused at base. Length: 1.0 cm. Diameter: 0.7 cm. Apex: Acute. Texture, upper and lower surfaces: Glabrous. Color, upper and lower surfaces: 146D at base, becoming 35C then 46B at margin.
- *Peduncle.*—Length: 12 cm. Diameter: 1.0 cm. Strength: Strong. Texture: Glabrous. Color: 200D.
- *Pedicels.*—Length: 0.5 cm. Diameter: 0.3 cm. Texture: Glabrous. Color: 147C.
- *Bracts.*—Bract number: One, sheathing the base of the outer-facing sepals. Bract shape: Ovate. Apex: Rounded. Margin: Entire. Base: Truncate. Arrangement: Subtending each flower. Length: 1.1 cm. Width: 1.2 cm. Texture: Glabrous. Color, upper and lower surfaces: Translucent, tinged pink 63C.
- *Staminodes.*—Modified stamens, comprising the showy part of the flower, (sterile petaloids). Quantity: 3 (excluding labellum). Staminode apex: Rounded. Margin: Entire, undulating. Base: Hastate. Length: 5.0 cm-6.5 cm. Width: 3.5 cm-5.0 cm. Shape: Spatulate. Color (both surfaces): 17A-17B except basal band (1.0 cm-1.5 cm) 13C.
- *Labellum* (*lower staminode*).—Labellum number: 1. Shape: Spatulate. Length: 6.5 cm. Width: 4.5 cm. Apex: Emarginate; notch up to 5 mm in depth. Margin: Entire. Base: Sheathing, truncate. Labellum surface color (both surfaces): 17A-17B with darker orange-red N30B longitudinal streaks more closely packed towards base.

Reproductive organs:

- *Petaloid stamen.*—One. Shape: Falcate. Dimensions: Length 8 cm, width 1.2 cm. Apex: Truncate. Base:

Truncate. Margin: Entire. Texture (both surfaces): Smooth. Color (both surfaces): 23A.

*Anther* (*fused to inward curved margin*).—Shape: Rectangular. Dimensions: Length 10 mm, width 2 mm. Color: (at dehiscence): 197D with two dark ribs 199C.

*Pollen.*—Amount: Moderate. Color: 4C.

*Petaloid style.*—One. Shape: Elongated spatulate.

*Dimensions.*—Length: 5 cm; width; 2 mm at base, widening to 5 mm at widest point then 3 mm at apex. Apex: Truncate. Base: Truncate. Margin: Entire. Texture (both surfaces): Smooth, shiny. Color (both surfaces): 16A.

*Stigma.*—One, located at tip of petaloid style, flattened, round, diameter 2-5 mm. Color: Translucent 11C.

*Ovary.*—Color N144D.

*Seed.*—Fertilization has not occurred in any of the observed plants. Ovules remain undeveloped.

The invention claimed is:

1. A new and distinct cultivar of *Canna* plant named 'CHOCOLATE SUNRISE' as described and illustrated herein.

* * * * *